United States Patent [19]

Frazin

[11] Patent Number: 5,190,045
[45] Date of Patent: Mar. 2, 1993

[54] METHOD AND DEVICE FOR DOPPLER-GUIDED AND IMAGED RETROGRADE CATHETERIZATION

[76] Inventor: Leon J. Frazin, 2106 North Dayton, Chicago, Ill. 60614

[21] Appl. No.: 669,052

[22] Filed: Mar. 14, 1991

Related U.S. Application Data

[63] Continuation-in-part of Ser. No. 413,953, Sep. 28, 1989, Pat. No. 5,038,789.

[51] Int. Cl.$^5$ ............................................. A61B 8/06
[52] U.S. Cl. ............................................. 128/662.06
[58] Field of Search ...................... 128/660.03, 662.05, 128/662.06

[56] References Cited

U.S. PATENT DOCUMENTS

| | | |
|---|---|---|
| 3,443,433 | 5/1969 | Liston et al. |
| 4,175,566 | 11/1979 | Millar |
| 4,237,729 | 12/1980 | McLeod et al. |
| 4,577,637 | 3/1986 | Mueller, Jr. |
| 4,587,972 | 5/1986 | Morantte .................. 128/660.03 |
| 4,637,401 | 1/1987 | Johnston |
| 4,665,925 | 5/1987 | Millar |
| 4,674,336 | 6/1987 | Johnston |
| 4,771,782 | 9/1988 | Millar |
| 4,771,788 | 9/1988 | Millar |
| 4,920,967 | 5/1990 | Cottonaro et al. |
| 4,947,852 | 8/1990 | Nassi et al. |
| 5,022,399 | 6/1991 | Biegeleisen .................. 128/662.06 |
| 5,038,789 | 8/1991 | Frazin .................. 128/662.06 |

Primary Examiner—Francis Jaworski

[57] ABSTRACT

A method and apparatus for Doppler-guided, imaged intravascular catheterization of a higher mammal includes inserting into a peripheral blood vessel a steerable catheter which has a Doppler ultrasound transceiver at its tip, generating from signals produced by the ultrasound transceiver a continuous indication of the direction of blood flow direction relative to the catheter tip, visually displaying the indications on a display monitor, and advancing the catheter towards the heart in accordance with the indication of blood flow direction until the catheter is positioned at a desired location within the circulatory system of the mammal, and once the catheter is located at a designated position, removing the ultrasound transceiver and replacing it with an ultrasonic imaging transducer for generating a two-dimensional image of the vascular area surrounding the transducer.

18 Claims, 2 Drawing Sheets

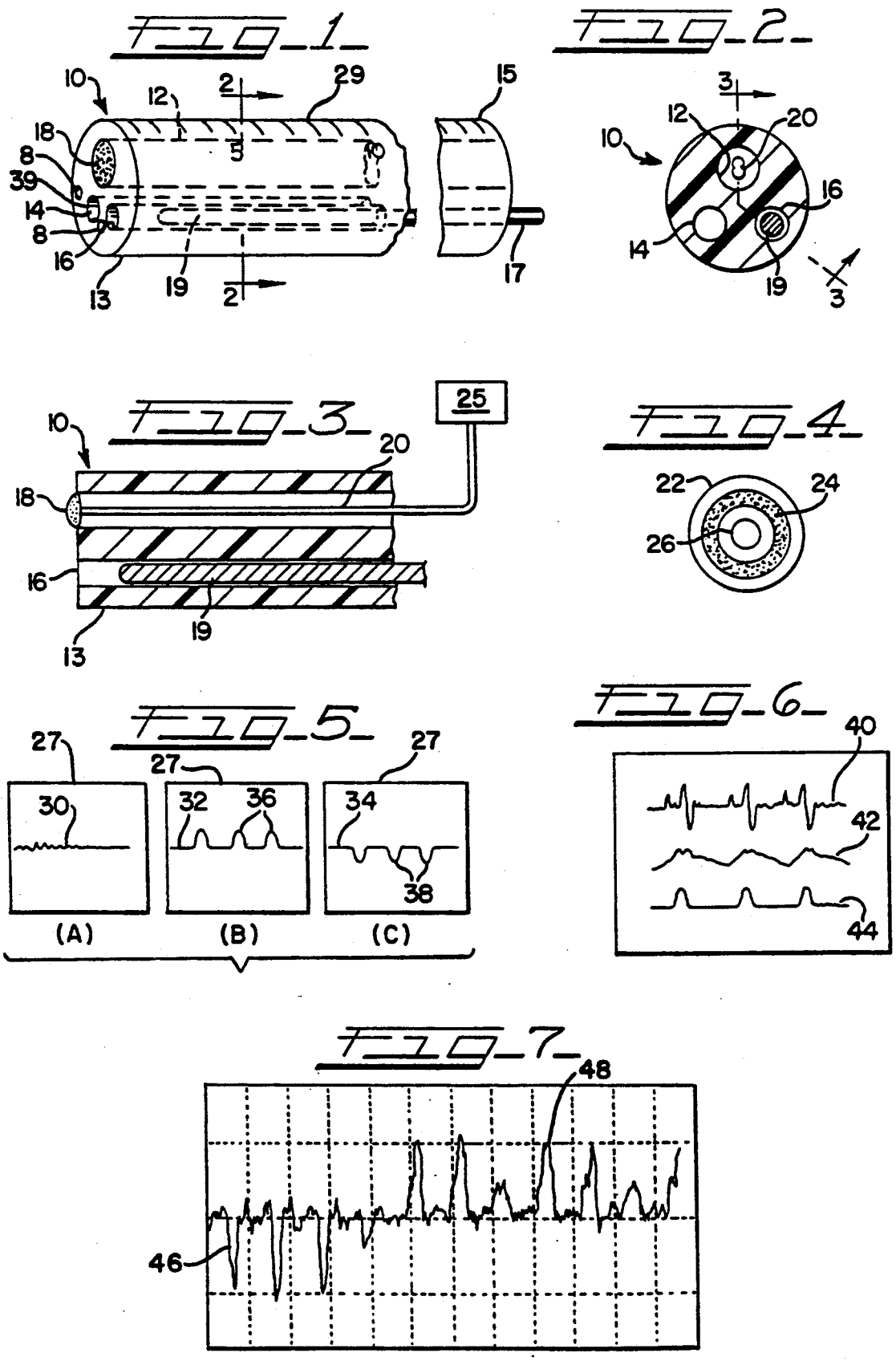

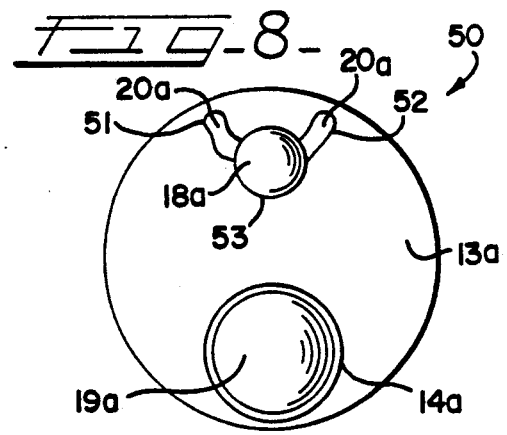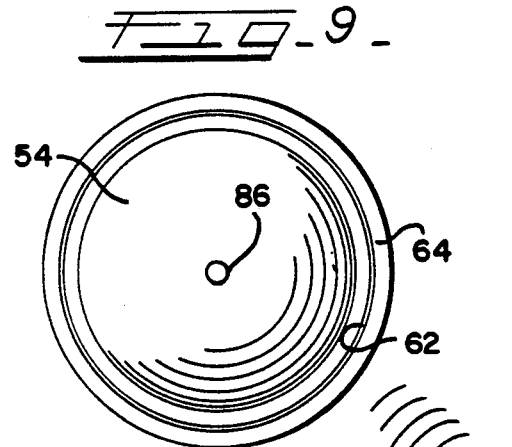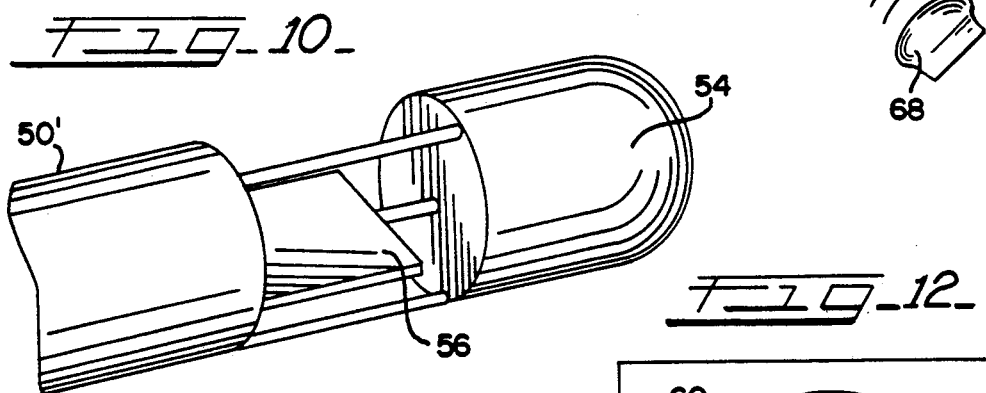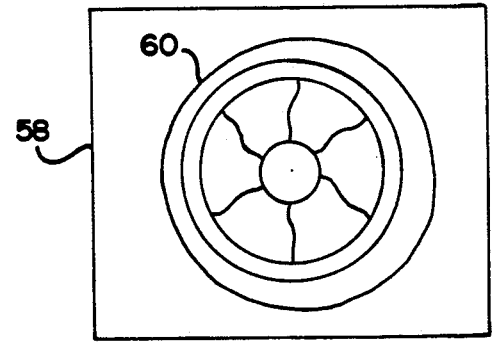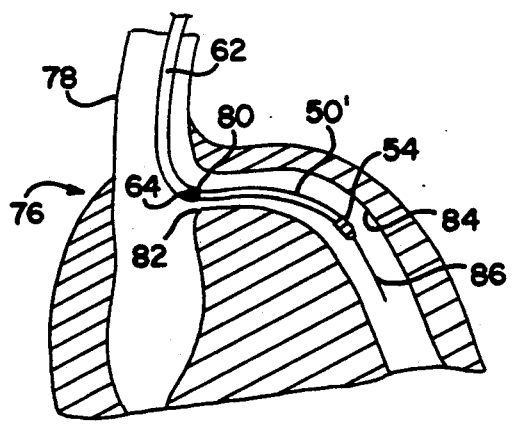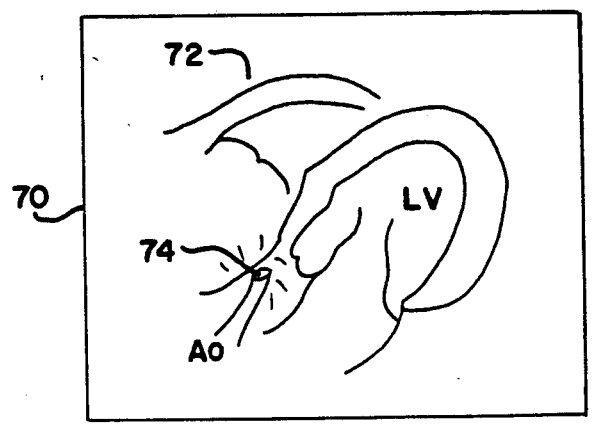

METHOD AND DEVICE FOR DOPPLER-GUIDED AND IMAGED RETROGRADE CATHETERIZATION

RELATED APPLICATION

This is a continuation-in-part of co-pending U.S. patent application Ser. No. 07/413,953, filed Sep. 28, 1989, for METHOD AND DEVICE FOR DOPPLER-GUIDED RETROGRADE CATHETERIZATION, now U.S. Pat. No. 5,038,789.

BACKGROUND OF THE INVENTION

The present invention relates to a procedure for the intravascular catheterization of higher mammals, and in particular to a method and device for imaged retrograde arterial catheterization without radiographic guidance. Specifically, the invention pertains to the use of a catheter-mounted Doppler ultrasound transceiver to selectively guide the cathether along the arterial tree towards the heart, and the use of an ultrasonic imaging transducer to generate an image of the area surrounding the catheter tip or at a point located distally therefrom.

Vascular catheterization is practiced medically for a variety of reasons, and is used in both diagnostic and therapeutic procedures. In the case of radioangiography, for example, the catheter is used to deliver a radiopaque dye to a desired point in the circulatory system. The dye is then injected and is passively distributed while being visualized via fluoroscopy or radiography, providing an indication of blood flow and distribution. Alternatively, the catheter may carry a device for the treatment of intra-vascular defects, such as an inflatable balloon which can be used to enlarge an area of vascular constriction.

Diagnostic devices can be attached to such catheters so as to allow the taking of intravascular measurements. It has been suggested elsewhere to attach an ultrasonic transceiver to a vascular catheter, either at or near its tip. Patents issued to Liston, et al. (U.S. Pat. No. 3,443,433), Millar (U.S. Pat. Nos. 4,175,566, 4,665,925, 4,771,782 and 4,771,788), McLeod, et al. (U.S. Pat. No. 4,237,729), and Johnston (U.S. Pat. Nos. 4,637,401 and 4,674,336) reveal the use of ultrasonic transceivers in conjunction with arterial or venous catheters. In all of these references, however, the ultrasonic element is introduced to measure blood flow velocity only.

Moreover, these references teach only conventional methods of positioning a catheter. The placement of a catheter into or near the left heart has, until now, been accomplished by fluoroscopically monitoring the catheter's progress through the circulatory system. The reference of Johnston (U.S. Pat. No. 4,637,401) proposes inserting the catheter in a vein and allowing it to be pulled downstream to the site of interest; this technique is unsuitable, however, for reaching the left heart chambers and the blood vessels immediately downstream.

Catheterization of the left heart requires upstream or retrograde insertion of a catheter and has typically involved the use of fluoroscopic equipment, which is unavoidably bulky and expensive and therefore restricts the available locations in which catheterizations can be performed. A further drawback of fluoroscopy-guided catheterization arises when the catheter is insufficiently radiopaque, requiring the use of radiopaque indicators or plugs inserted at the catheter tip, as suggested in U.S. Pat. No. 4,577,637. Yet another shortcoming is the undesirable exposure of the patient to radiation over long time periods, which necessarily occurs during fluoroscopy and which may pose a health risk as in the case of a pregnant patient. Still another drawback is the inability of conventional catheterization systems to accurately locate the specified position of the catheter tip in the heart or other area of the circulatory system, or to provide an image of the immediate area surrounding the catheter tip.

SUMMARY OF THE INVENTION

It is therefore an object of the invention to overcome these and other difficulties associated with fluoroscopy-guided left heart catheterization. This object is attained by the method of the present invention, in which a catheter having a Doppler ultrasound transceiver at its tip is advanced while a continuous signal generated by the transceiver is monitored by the physician or technician. By observing signal characteristics which are indicative of blood flow direction, the operator is able to steer the catheter in the retrograde direction at each arterial branch, thereby eventually reaching the heart.

The inventive catheterization method has the advantage that no fluoroscopy or radiography is required to correctly position the catheter tip in or near the left heart. Instead of using a cumbersome fluoroscopic apparatus, the physician or cardiac catheterization technician can perform the procedure using a readily portable control device having an oscilloscope-type monitoring screen.

Another advantage of the inventive method is that catheters need not be modified or equipped with radiopaque elements to enhance their fluoroscopic visibility. Furthermore, the patient is not exposed to radiation during the procedure, allowing catheterizations to be performed on individuals for whom a fluoroscopically-guided catheterization is contraindicated.

In addition, an ultrasonic imaging transducer, disposed at or near a catheter tip, may be used to provide a two-dimensional visual image of the area surrounding the tip or distally therefrom so as to facilitate the placement of the catheter in various portions of the circulatory system. Furthermore, the imaging transducer may be advanced into specified areas within the heart, such as into the coronary artery. If desired, the present catheter may be inserted into a flexible sheath having a transponder ring at its tip to facilitate the determination of the location of the catheter within the body by an esophageal or extracorporeal ultrasonic transducer.

These and other benefits of the present invention will be understood more clearly in connection with the following detailed description.

BRIEF DESCRIPTION OF THE DRAWINGS

The invention is described with reference to several drawings, in which;

FIG. 1 is a perspective view of a multiple-lumen catheter suitable for use in the method of the present invention;

FIG. 2 is a cross-sectional view of the catheter of FIG. 1, taken along line 2—2 of FIG. 1 and in the direction generally indicated;

FIG. 3 is a longitudinal section of the catheter of FIG. 1, taken along line 3—3 of FIG. 2 and in the direction generally indicated;

FIG. 4 is an end view of an alternative catheter configuration;

FIGS. 5A-C are representative displays on a monitor used in the method of the present invention, showing tracings indicative of various positionings of the catheter tip;

FIG. 6 is a representative multi-functional display on a monitor used in the method of the present invention;

FIG. 7 is a representative monitor display used in the method of the present invention, showing tracings indicative of various positionings of the catheter tip as it advances through the femoral artery of a dog;

FIG. 8 is an end view of an alternate embodiment of a catheter suitable for use with the present invention;

FIG. 9 is an end view of a catheter suitable for use with the present method and having a two-dimensional scanning type ultrasonic imaging transducer inserted therein;

FIG. 10 is a fragmentary top perspective view of the two-dimensional scanning imaging transducer shown in FIG. 9;

FIG. 11 is a diagrammatic sectional view of a portion of the human heart in which the present method may be practiced with the catheter of FIG. 9;

FIG. 12 is a diagrammatic view of the monitor display generated by the catheter of FIG. 9 employing the transducer of FIG. 10; and FIG. 13 is a diagrammatic view of the monitor display generated by an external ultrasonic transducer used with the catheter of FIG. 9.

DESCRIPTION OF THE PREFERRED EMBODIMENT

The inventive method is herein described primarily in connection with catheterization of the left heart; however, it should be apparent that other procedures are likewise possible using Doppler-guided catheterization A steerable catheter 10 is shown in FIGS. 1-3. Catheter 10 is a multiple-lumen catheter of well-known type, and has a first lumen 12 which is capped at its tip or distal end 13 with a Dopler-type ultrasound transceiving crystal 18. Electrical leads 20 extend from the transceiver 18, through the length of lumen 12, to a conventional external power supply and control apparatus 25. If desired, the electrical leads 20 from crystal 18 can extend through two separated lumens, thereby eliminating the possibility of an electrical short circuit.

A second lumen 14 is hollow and at its proximal end 15 is provided with a connector 17 which allows the attachment of a variety of instruments, such as a manometric device for obtaining measurements of blood pressure at the catheter tip 13 or a syringe for the injection of contrast media or therapeutic compounds. Lumen 14 may include two or more side holes 8 (best seen in FIG. 1) near the tip 13 for echo contrast injection. A third lumen 16 accommodates a guide wire 19 which may be of a J-tipped or other suitable type, with which the operator can steer the catheter 10 during insertion.

Other catheter configurations may also be suitable for the use with the method of the present invention. The above-described catheter 10 has a diameter of approximately 7-8 French (F), or approximately 2.5 mm. Narrower catheter diameters of 5-7 F are attainable by using a two-lumen catheter, in which a guide wire is fitted into the same lumen used for pressure measurement. A readily available Y-connector is then used at the proximal catheter port to allow both guide wire manipulation and pressure readings.

Even narrower catheters may be used which have only one lumen. One such catheter 22 is shown in FIG. 4, and has a ring-shaped Doppler transceiver 24 surrounding a single lumen 26 which is used for both pressure measurement and a guide wire. In the case of catheter 22, the electrical leads attached to transceiver 24 may be embedded in the wall of the catheter.

The Doppler ultrasound control apparatus or unit 25, which is connected to the transceiver 18 by leads 20, serves as a power supply for the transceiver which generates an ultrasound signal of approximately 20 megahertz. The apparatus 25 also processes signals produced by the transceiver 18, and displays those signals as a tracing on an oscilloscope-type monitor 27 (best seen in FIG. 5), to which the control apparatus is electrically connected.

The catheter 10 is demarcated in centimeters 29 to identify the distance from the arterial insertion site. The guide wire 19 is also similarly demarcated in centimeters to identify the distance that the end of the wire extends out of the catheter tip 13.

In the case of a cardiac catheterization, the catheter 10 is inserted into the brachial or, preferably, the femoral artery using a suitable insertion sheath (not shown). The catheter 10 is directed in the retrograde direction, i.e., against the flow of blood. This orientation of the catheter tip 13 is indicated by a shift in the display on the monitor 27 from the tracing 20 of FIG. 5a, which coincides with zero blood flow, to the tracing 32 of FIG. 5b. The appearance of upwardly-directed peaks 36 on the display is representative of blood flow towards the Doppler transceiver during systole (i.e., contraction of the left ventricle). This is in contrast to the monitor display of FIG. 5c, in which blood flows away from the transceiver and produces systolic peaks 38 of tracing 34 which are directed downwardly.

The catheter 10 is next advanced through the arterial tree towards the heart while the monitor display 27 is watched for any change in the tracing configuration. Should the operator accidentally guide the catheter 10 into an incorrect arterial branch, the monitor tracing 30, 32, 34 will show a downward deflection during systole instead of an upward one, indicating that the direction of catheter advancement is no longer retrograde. The catheter 10 is then withdrawn slightly, and rotated with possible guide wire adjustment. In this manner, the catheter 10 is maneuvered into the correct vessel. Alternatively, the catheter 10 may be advanced without the use of the guide wire 19. The catheter 10 may have sufficient rigidity and be of appropriate shape for some patients to permit advancement by manual force and slight periodic rotation.

The catheter 10 is advanced until the aortic arch or a position superior to the aortic valve is reached. Guidance and positioning of the catheter are facilitated by monitoring the blood pressure at the catheter tip 13, using a manometric transducer 39 connected to the open lumen 14. Advantageously, the output of the transducer 39 as well as the patient's electrocardiograph (EKG) and the Doppler transceiver signal may be simultaneously displayed on a single monitor as shown in FIG. 6, in which tracings 40, 42, and 44 correspond to the EKG, pressure and Doppler ultrasound signals, respectively.

The final positioning of the catheter tip 13 can be accomplished by any of a number of non-fluoroscopic techniques. Guide wire manipulation may help crossing the aortic valve so as to enter the left ventricular chamber. The operator may be able to rely on pressure readings to establish that the left heart ventricle has been reached. If desired, an external or esophageal ultrasound transducer may be used in conjunction with a transponder to accurately locate the catheter tip 13. This second ultrasound transducer may also be used to observe the location of the metallic catheter tip within the heart.

Once the catheter 10 has been properly placed, a variety of procedures may be carried out using the open catheter lumen 14 (as, for example, the measurement of left ventricular pressures or the injection of echogenic contract materials for myocardial ultrasound perfusion analysis and valvular regurgitation analysis). In other cases, such as where a different type of catheter is needed, the Doppler-guided catheter 10 may be withdrawn while leaving the guide wire 19 in place. The desired catheter is then inserted over the guide wire 19, and the guide wire withdrawn if necessary. In this fashion, the present method can be used to place any type of catheter in or near the heart.

The advantages of the present method are further apparent in the case of a patient having a stenotic aortic valve. Cardiac catheterization is frequently difficult because of the partially occluded condition of such a valve. Using the present Doppler-guided catheter 10, however, the operator is readily able to identify the exact location and timing of peak flow through even a badly stenosed valve, and to insert the catheter tip 13 into the left heart. Likewise, the present method works well even in cases of arterial narrowing as by atherosclerosis, as the increased blood velocity through the affected vessel enhances the upward deflection of the ultrasound tracing. The catheter could also be used for guidance placement for an intra-aortic balloon pumping device.

The doppler wave form in the aorta could also be used to calculate stroke volume and therefore cardiac output (requires knowledge of aortic root diameter, which can be obtained with standard echocardiographic techniques).

Although the description of the above method pertains to cardiac catheterization, it should be noted that Doppler-guided retrograde catheterization can be used equally well in studies of blood vessels or organs intermediate to the point of catheter insertion and the heart. For example, ultrasonic angiography of the iliac or renal arteries can be conducted by advancing the catheter tip just beyond the junction of the abdominal aorta and the artery in question. Using an external ultrasound transducer in combination with a transponder, the catheter is positioned precisely and used to inject echogenic contrast material. Similary, blood flow in the carotid arteries can be studied by choosing an appropriate injection point in the aortic arch. A further possible use of this method is in venous anterograde catheterization, in which a Doppler-guided catheter is inserted in a suitable vein and advanced downstream towards the vena cava and right heart.

EXAMPLE I

The above method was used in performing the Doppler-guided left heart catheterization of dogs.

A Doppler flow catheter was inserted through the femoral artery of the dog. The monitor display showed that the tracing 46 on the left side of the graph (see FIG. 7) consisted of downwardly directed peaks below the base line which indicated that the blood flow was going toward the transducer, signifying that the guide catheter was being advanced in the correct direction. The right side of the graph of FIG. 7 showed upwardly directed peaks 48 above the base line which indicated that the guide catheter had been inadvertently advanced into the wrong vessel.

FIG. 7 shows a tracing 46, 48 having downwardly directed peaks which indicates that the blood flow was going toward the transducer as compared to FIGS. 5 and 6 which show the inverse. This difference between FIGS. 5, 6, and FIG. 7 was due to a change in the polarity of equipment used in the respective tests. Responsive to an abnormal tracing on the monitor display, as indicted in the above example, the catheter was slightly withdrawn from the artery, rotated and advanced in the direction where there was positive flow towards the transducer.

Following catheterization of the test animals, fluoroscopy was used to confirm that the catheter tip had been successfully positioned.

Referring now to FIG. 8, an alternate embodiment of the catheter of the invention is indicated generally at 50. The catheter 50 is generally of the same design as is the catheter 10, and as such identical components will be assigned identical reference numerals, with the addition of the subscript "a". Hence, the lumen 14 becomes 14a, etc. Thus, the catheter 50 includes a Doppler transceiver 18a to which are connected a pair of lead wires 20a, each of which is inserted through a corresponding upper lumen 51, 52. The lead wires 20a are placed in separate lumens to prevent short circuits. In the preferred embodiment, the lumens 51, 52 are relatively smaller in diameter than the larger lower lumen 14a. It is also preferred that the transceiver 18a is configured to nest within a hemispherical recess 53 in the catheter tip 13a. The transceiver 18a is thus prevented from becoming detached from, or misaligned upon, the catheter tip 13a. The lumen 14a may be equipped with a guide wire 19a and/or a pressure transducer (not shown).

The catheter 50 having the Doppler transceiver 18a may be used with a catheter sheath, and may be withdrawn from the sheath and replaced by a catheter 50' having an ultrasonic imaging transducer 54 inserted therein (best seen in FIGS. 10 and 11). The transucer 54 is preferably of the high frequency (approximately 30-50 MHz), two-dimensional scanning type. The scanning may be accomplished by a rotating reflector 56 as is known in the art, by a conventional phased array scanner, as well as by other similarly effective scanning devices. The transducer 54 is disposed at the end of catheter 50' to provide a two-dimensional image of the portion of the heart or other region of the circulatory system which directly surrounds the tip of catheter 50'. In addition, the transducer 54 is preferably electrically connected to a monitor 58 (best seen in FIG. 12) so as to create a two-dimensional image display 60.

Referring now to FIG. 9, it has been found that in order to obtain the maximum benefit of the above-described retrograde catheterization and imaging technique, it is advisable for the operator to be fairly certain of the exact location of the catheter tip within the circulatory system. To this end, the catheters 50 and 50' may be fabricated to be of sufficiently small dimension to be slidably inserted into a flexible catheter guiding sheath 62 as is known in the art. The sheath 62 may be equipped with a transponder 64, which may be configured as a ring annularly disposed around the periphery of the sheath 62. If desired, the transponder 64 may be located near the tip of the catheter 50'.

Referring now to FIGS. 9 and 13, the transponder 64 senses a pulsating ultrasonic signal which is emitted by an ultrasonic transducer 68 located outside the body. Signals generated by both the transponder 64 and the transducer 68 are integrated so as to generate on a monitor 70 a two-dimensional display image 72 of a region of the heart in which the tip of the sheath 62 is located. The action of the impulses sensed by the transponder 64 creates a flashing or similar marker display 74 on the display 72 of the monitor 70. In this manner, the precise position of the catheter tip 13a and the tip of the sheath 62 may be discerned. By visually monitoring the displays 60 and 72, the operator may accurately guide the sheath 62 into specified areas of the heart, such as the coronary ostium, so that ultrasonic contrast media may be administered, and/or that the catheter 50' can be advanced into the coronary artery to image the arterial walls.

Referring now to FIG. 11, a partial cross-sectional view of the heart is depicted in which the heart is generally designated 76. Blood is pumped from the heart 76 via the ascending aorta 78, which is also the vessel into which the sheath 62, containing the catheter 50, is guided in the retrograde direction through the use of the Doppler transceiver 18a and as described above in relation to FIGS. 1-6, 8, 9 and 13. Ultimately, the tip 80 of the sheath 62 is positioned at the entrance 82 of the coronary artery 84.

At this time, the catheter 50 bearing the Doppler transceiver 18a is withdrawn from the sheath 62 and is replaced by the catheter 50' bearing the ultrasonic imaging transducer 54 (best seen in FIGS. 9 and 10). The catheter 50' is then inserted into the sheath 62 until it reaches the tip 80. The transducer 54 is manipulated into the coronary artery 84 through the use of a guide wire 86 mounted at the tip of the transducer 54. As it progresses, and through the rotation of the reflector 56, the transducer 54 provides the continuous image 60 of the condition of the interior of the arterial wall. It is also contemplated that the transceiver 18a and the transducer 54 may be combined into a single catheter.

Referring now to FIG. 12, if desired, the image display 60 may be combined with the displays 40, 42, 44 and 72 (best seen in FIGS. 6 and 13), either on an adjacent monitor 58, or on the same monitor 27. If the transponder 64 is provided, the various monitored parameters may thus be incorporated into a single instrument console to enable continuous and accurate monitoring of the position of the catheter tip 13a in the circulatory system. Naturally, due to the limited number of lumens such as 51, 52 and 14a in the catheter 50 (and lumens 12 and 14 in the catheter 10) as presently described, it may not be possible to monitor all of the functions simultaneously.

Thus, through the use of the catheter 50, the Doppler transceiver 18a is used as a locating mechanism to advance in the retrograde direction and position the catheter at a specified portion of the heart, such as at the entry way of the coronary artery. Once the tip 13a of the catheter 50 is properly located by means of the above-described Doppler-guided retrograde catheterization (with the possible assistance of associated transponder technology), the ultrasonic transducer 54 may be used to observe the condition of arterial walls, including the walls of the coronary artery. A significant advantage of the present system is that the heart may be catheterized without the use of X-rays or other fluoroscopic techniques.

The above description of the inventive method are for the purpose of better illustrating its use, and are not intended to limit the scope of the invention. It will be appreciated by those familiar with the art that variations in the materials and techniques described herein are within the ambit of the claims which follow.

I claim:

1. A method for the Doppler-guided, imaged intravascular catheterization of a higher mammal, comprising:

inserting into a peripheral blood vessel a catheter having a tip having an ultrasound transceiver operationally disposed therewith;

generating from signals produced by the ultrasound transceiver a continuous indication of the direction of blood flow relative to the catheter;

displaying said indication of blood flow direction;

advancing the catheter towards the heart in accordance with the indication of blood flow direction;

locating the catheter at the coronary ostium using a transponder and an external ultrasonic transducer; and providing an ultrasonic imaging transducer to generate an image of the location of the vessel surrounding said transducer.

2. The method of claim 1 wherein the ultrasonic imaging transducer is provided by replacing said catheter bearing the ultrasound transceiver with a catheter having an ultrasonic imaging transducer.

3. The method of claim 2 wherein the said ultrasonic imaging transducer is advanced into a blood vessel and generates a visual image of the vessel wall.

4. The method of claim 2 wherein said catheter bearing the ultrasound transceiver is provided in a sheath having said transponder associated therewith, and further including withdrawing said catheter from said sheath and inserting said catheter bearing the imaging transducer.

5. The method of claim 4 wherein said catheter bearing said imaging transducer is slidably advanced beyond said sheath into the coronary artery.

6. The method of claim 4 wherein said transponder has a ring configuration.

7. The method of claim 1 wherein said imaging transducer is provided with a guide wire.

8. A method for the Doppler-guided, imaged catheterization of a human patient comprising:

inserting a catheter into a peripheral artery selected from the group consisting of the brachial and femoral arteries, the catheter having a tip and a Doppler ultrasound transceiver disposed at said tip, said catheter being slidably inserted in a sheath;

generating from signals produced by said ultrasound transceiver a continuous indication of the direction of blood flow relative to said catheter tip;

visually displaying said indications of blood flow direction;

advancing said catheter and said sheath towards the heart in the retrograde direction in accordance with said indications of blood flow direction while steering said catheter;

selectively positioning said catheter tip at a desired location within the circulatory system of the patient;

withdrawing said Doppler transceiver from said sheath and inserting into said sheath a second catheter having an ultrasonic imaging transducer;

advancing said imaging transducer into the coronary artery; and generating ultrasonic signals of the area surrounding said transducer by means of said ultrasonic imaging transducer to observe the condition of the coronary artery.

9. The method of claim 8 further including visually displaying the signals generated by the ultrasonic imaging transducer.

10. The method of claim 8 further including providing said sheath with a transponder which senses pulsing ultrasonic impulses.

11. The method of claim 10 wherein said transponder is located on the tip of said sheath into which the catheter is inserted.

12. The method of claim 10 further including an ultrasonic transducer located external to the patient for monitoring the signals sensed by said transponder.

13. A device for the Doppler-guided, imaged intravascular catheterization of a higher mammal comprising:

a first catheter capable of insertion into a peripheral blood vessel and having a tip, at least one lumen, and a proximal end;

a sheath into which said catheter is slidably inserted;

an ultrasonic transceiver disposed at said catheter tip and associated with the one of said lumens, said transceiver being capable of producing an electrical signal indicative of the direction of blood flow relative to said catheter;

an ultrasonic imaging transducer configured for association with a second catheter for insertion into said sheath upon the withdrawal of said first catheter therefrom, said imaging transducer being capable of generating ultrasonic signals of the area surrounding said imaging transducer; and at least one display monitor visible to an operator of the device, said at least one display monitor being electrically connected to the ultrasonic transceiver and to said transducer, said at least one display monitor being capable of visually displaying the indication of blood flow direction generated by said transceiver and a visual image generated by said transducer.

14. The device of claim 13 additionally comprising a guide wire inserted into a lumen of said first catheter and capable of manipulation independently of said catheter.

15. The device of claim 13 wherein said imaging transducer has a guide wire attached thereto.

16. The device of claim 13 wherein said sheath is provided with a transponder.

17. The device of claim 16 further including a second ultrasonic transducer located outside the body for receiving signals sensed by said transponder.

18. The device of claim 16 wherein said transponder is configured as a ring and is located at the tip of a guiding sheath into which said catheter is inserted.

* * * * *